United States Patent
Hof et al.

(10) Patent No.: US 10,492,935 B2
(45) Date of Patent: Dec. 3, 2019

(54) PHASE-CHANGE MATERIALS

(71) Applicant: NEW PHASE LTD., Givat Shmuel (IL)

(72) Inventors: Refael Hof, Kfar-Yona (IL); Valery Perevalov, Kfar Saba (IL)

(73) Assignee: NEW PHASE LTD, Givat Shmuel (IL)

( * ) Notice: Subject to any disclaimer, the term of this patent is extended or adjusted under 35 U.S.C. 154(b) by 1143 days.

(21) Appl. No.: 14/579,340

(22) Filed: Dec. 22, 2014

(65) Prior Publication Data

US 2015/0112423 A1    Apr. 23, 2015

Related U.S. Application Data

(63) Continuation of application No. 13/392,037, filed as application No. PCT/IL2010/000683 on Aug. 22, 2010, now Pat. No. 9,572,695.

(Continued)

(51) Int. Cl.
*A61F 2/02*     (2006.01)
*A61F 2/94*     (2013.01)
(Continued)

(52) U.S. Cl.
CPC ............... *A61F 2/94* (2013.01); *A61B 18/04* (2013.01); *A61F 2/02* (2013.01); *A61F 2/04* (2013.01); *A61F 7/12* (2013.01); *A61F 2/91* (2013.01); *A61F 2007/0292* (2013.01); *A61F 2210/008* (2013.01); *A61F 2210/0014* (2013.01); *A61F 2210/0061* (2013.01); *A61F 2210/0066* (2013.01); *A61F 2250/0001* (2013.01); *A61F 2250/0067* (2013.01); *A61N 1/086* (2017.08);

(Continued)

(58) Field of Classification Search
CPC ........ A61F 2/94; A61F 7/12; A61F 2210/008; A61F 2007/0292; A61F 2250/0001; A61B 18/04

See application file for complete search history.

(56) References Cited

U.S. PATENT DOCUMENTS 4,096,616 A    6/1978  Coffinberry
4,106,488 A    8/1978  Gordon
(Continued)

FOREIGN PATENT DOCUMENTS

CN    1724135        1/2006
CN    1018336915     9/2010
(Continued)

OTHER PUBLICATIONS

European Search Report dated Jul. 9, 2015, which issued during the prosecution of Applicant's European App No. 14192528.9.

(Continued)

*Primary Examiner* — Kaitlyn E Smith
*Assistant Examiner* — Yasamin Ekrami
(74) *Attorney, Agent, or Firm* — Sughrue Mion, PLLC

(57) ABSTRACT

A method is provided, including, delivering into a heart of a patient an annuloplasty ring structure including a body portion and an adjusting mechanism configured to adjust a size of the body portion of the annuloplasty ring structure, the adjusting mechanism including a housing, and following the delivering, moving the housing with respect to the body portion. Other applications are also described.

6 Claims, 5 Drawing Sheets

Related U.S. Application Data

(60) Provisional application No. 61/275,071, filed on Aug. 24, 2009, provisional application No. 61/275,089, filed on Aug. 24, 2009, provisional application No. 61/275,068, filed on Aug. 24, 2009.

(51) Int. Cl.

| | |
|---|---|
| A61F 7/12 | (2006.01) |
| A61B 18/04 | (2006.01) |
| A61F 2/04 | (2013.01) |
| A61F 2/91 | (2013.01) |
| A61N 1/40 | (2006.01) |
| A61N 7/00 | (2006.01) |
| A61F 7/02 | (2006.01) |
| A61N 1/08 | (2006.01) |

(52) U.S. Cl.
CPC ...... *A61N 1/406* (2013.01); *A61N 2007/0039* (2013.01)

(56) References Cited

U.S. PATENT DOCUMENTS

| | | | |
|---|---|---|---|
| 4,204,573 | A | 5/1980 | Clark |
| 4,392,040 | A | 7/1983 | Rand et al. |
| 4,440,217 | A | 4/1984 | Stieler |
| 4,569,836 | A | 2/1986 | Gordon |
| 4,678,460 | A | 7/1987 | Rosner |
| 4,747,826 | A | 5/1988 | Sassano |
| 4,983,159 | A | 1/1991 | Rand |
| 5,003,991 | A | 4/1991 | Takayama |
| 5,217,363 | A | 6/1993 | Brais et al. |
| 5,317,506 | A | 5/1994 | Coutre et al. |
| 5,385,540 | A | 1/1995 | Abbott et al. |
| 5,545,210 | A | 8/1996 | Hess et al. |
| 5,658,234 | A | 8/1997 | Dunlavy |
| 5,667,522 | A | 9/1997 | Flomenblit et al. |
| 5,716,410 | A | 2/1998 | Wang et al. |
| 5,830,179 | A | 11/1998 | Mikus et al. |
| 5,964,744 | A | 10/1999 | Balbierz et al. |
| 5,984,893 | A | 11/1999 | Ward |
| 6,059,810 | A | 5/2000 | Brown et al. |
| 6,120,534 | A | 9/2000 | Ruiz |
| 6,323,459 | B1 | 11/2001 | Maynard |
| 6,390,185 | B1 | 5/2002 | Proeschel |
| 6,451,044 | B1 | 9/2002 | Naghavi et al. |
| 6,576,001 | B2 | 6/2003 | Werneth et al. |
| 6,746,439 | B2 | 6/2004 | Lenker |
| 6,768,921 | B2 | 7/2004 | Organ et al. |
| 6,805,711 | B2 | 10/2004 | Quijano et al. |
| 6,835,858 | B1 | 12/2004 | De Jonge et al. |
| 6,942,637 | B2 | 9/2005 | Cartledge et al. |
| 6,942,644 | B2 | 9/2005 | Worthen |
| 7,041,941 | B2 | 5/2006 | Faries, Jr. et al. |
| 7,074,175 | B2 | 7/2006 | Handy |
| 7,112,273 | B2 | 9/2006 | Weigel et al. |
| 7,117,033 | B2 | 10/2006 | Shalev et al. |
| 7,120,489 | B2 | 10/2006 | Shalev et al. |
| 7,146,209 | B2 | 12/2006 | Gross et al. |
| 7,510,555 | B2 | 3/2009 | Kanzius |
| 7,560,160 | B2 | 7/2009 | Sudarshan |
| 7,627,381 | B2 | 12/2009 | Kanzius |
| 7,731,648 | B2 | 6/2010 | Ivkov |
| 7,919,184 | B2 | 4/2011 | Mohapatra |
| 8,197,471 | B1 | 6/2012 | Tersigni |
| 8,463,397 | B2 | 6/2013 | Munoz Marquez |
| 8,518,870 | B2 | 8/2013 | Harrison, Jr. |
| 8,709,488 | B2 | 4/2014 | Peyman |
| 9,872,902 | B2 | 1/2018 | Hof et al. |
| 2002/0183829 | A1 | 12/2002 | Doscher |
| 2004/0059385 | A1 | 3/2004 | Yu |
| 2004/0122494 | A1 | 6/2004 | Eggers et al. |
| 2004/0180086 | A1 | 9/2004 | Ramtoola et al. |
| 2004/0210269 | A1 | 10/2004 | Shalev et al. |
| 2004/0253304 | A1 | 12/2004 | Gross et al. |
| 2005/0033382 | A1* | 2/2005 | Single ............. A61N 1/375 607/57 |
| 2005/0055082 | A1 | 3/2005 | Ben Muvhar et al. |
| 2005/0059928 | A1 | 3/2005 | Larsson |
| 2005/0074506 | A1 | 4/2005 | Natan et al. |
| 2005/0080351 | A1 | 4/2005 | Larsson |
| 2005/0090732 | A1 | 4/2005 | Ivkov et al. |
| 2005/0149170 | A1* | 7/2005 | Tassel ............. A61B 5/0031 623/1.15 |
| 2005/0159790 | A1 | 7/2005 | Shalev |
| 2005/0202310 | A1* | 9/2005 | Yahnker ............. B25F 5/008 429/62 |
| 2005/0283327 | A1 | 12/2005 | Bowman et al. |
| 2005/0288777 | A1 | 12/2005 | Rhee et al. |
| 2006/0020299 | A1 | 1/2006 | Shalev |
| 2006/0074479 | A1 | 4/2006 | Bailey et al. |
| 2006/0083694 | A1 | 4/2006 | Kodas |
| 2006/0194164 | A1* | 8/2006 | Altshuler ............. A46B 9/04 433/29 |
| 2006/0241747 | A1 | 10/2006 | Shaoulian et al. |
| 2006/0276882 | A1 | 12/2006 | Case et al. |
| 2007/0083245 | A1 | 4/2007 | Lamensdorf et al. |
| 2007/0154397 | A1 | 7/2007 | Chang et al. |
| 2007/0264481 | A1 | 11/2007 | DeSimone et al. |
| 2008/0021537 | A1 | 1/2008 | Ben Muvhar et al. |
| 2008/0033509 | A1 | 2/2008 | Shalev et al. |
| 2008/0167700 | A1 | 7/2008 | Shalev et al. |
| 2008/0172102 | A1 | 7/2008 | Shalev |
| 2008/0272331 | A1 | 11/2008 | Mohaparta et al. |
| 2009/0082832 | A1 | 3/2009 | Carbunaru et al. |
| 2010/0256708 | A1* | 10/2010 | Thornton ............. A61N 1/375 607/61 |
| 2011/0195526 | A1 | 8/2011 | Su |
| 2013/0078288 | A1 | 3/2013 | Yu |
| 2015/0231282 | A1 | 8/2015 | Pozzo et al. |

FOREIGN PATENT DOCUMENTS

| | | |
|---|---|---|
| DE | 19745890 C1 | 3/1999 |
| EP | 0543498 A1 | 5/1993 |
| JP | 03178668 | 8/1991 |
| JP | 2003509098 A | 3/2003 |
| JP | 2003527924 A | 9/2003 |
| JP | 2008515468 A | 5/2008 |
| WO | 94/001165 | 1/1994 |
| WO | 97/26032 | 7/1997 |
| WO | 2000/066192 | 11/2000 |
| WO | 0119239 A1 | 3/2001 |
| WO | 0172239 A2 | 10/2001 |
| WO | 02/000145 | 1/2002 |
| WO | 03/028522 | 4/2003 |
| WO | 03/105658 | 12/2003 |
| WO | 2006052322 A2 | 5/2006 |
| WO | 2007/107762 | 9/2007 |
| WO | 2008148014 A2 | 12/2008 |
| WO | 2009012473 A2 | 1/2009 |
| WO | 2011/024159 | 3/2011 |

OTHER PUBLICATIONS

An Office Action dated Jun. 27, 2017, which issued during the prosecution of Japanese Patent Application No. 112337/2016.
An Office Action dated Apr. 8, 2015, which issued during the prosecution of U.S. Appl. No. 13/392,037.
Communication dated Jan. 4, 2015, issued by the Israel Patent Office in corresponding application No. 218247.
Communication dated Mar. 13, 2015, issued by the European Patent Office in corresponding application No. 14192528.9.
An Office Action dated Dec. 11, 2015, which issued during the prosecution of U.S. Appl. No. 13/392,037.
An Extended European Search Report dated Mar. 8, 2013, which issued during the prosecution of European Patent Application No. 10811360.
Database Impact [Online] the institute of electrical engineers, Stevenage, GB: Jan. 1, 2009, Huang Yong et al., "Preparation and

(56) References Cited

OTHER PUBLICATIONS

Characterization of magnetic phase-change microcapsules", XP002693430 Database accession No. 11184663 (abstract).
Notice of Reasons for Refusal, dated Apr. 8, 2014, issued by the Japanese Patent Office, in counterpart Application No. 2012-526180.
Int. J. Hyperthermia, 2005, 1-11, preview article, by Johannsen et al. "Clinical hyperthermia of prostate cancer using magnetic nanoparticles: Presentation of a new interstitial technique" Published: Nov. 2005.
De Jong et al. "Particle size-dependent organ distribution of gold nanoparticles after intravenous administration" Published: Feb. 2008 Biomaterials 29 (2008) 1912-1919.
"Energy Absorption of Gold Nanoshells in Hyperthermia Therapy" Published: Aug. 2008 NanoBioscience, IEEE Transactions on, Issue Date: Sep. 2008, Written by: Changhong Liu; Mi, C.C.; Li, B.Q.
Robby Petros et al. "Strategies in the design of nanoparticles for therapeutic applications" Published: Jul. 2010 Nature Reviews Drug Discovery 9, 615-627 (Aug. 2010).
Shenoi et al."Nanoparticle Pre-Conditioning for Enhanced Thermal Therapies in Cancer" Published: Apr. 2011 Nanomedicine (Lond). Apr. 2011; 6(3): 545-563.
Yonggang Lv, et al. "Theoretical model for thermal protection by microencapsulated phase change micro/nanoparticles during hyperthermia" Published: Sep. 2011 Heat Mass Transfer (2012) 48:573-584.
Communication dated Aug. 19, 2014 in related U.S. Appl. No. 13/392,037.
U.S. Appl. No. 61/275,068, filed Aug. 24, 2009.
U.S. Appl. No. 61/275,071, filed Aug. 24, 2009.
U.S. Appl. No. 61/275,089, filed Aug. 24, 2009.
An International Preliminary Report on Patentability dated Feb. 28, 2012, which issued during the prosecution of Applicant's PCT/IL2010/000683.
International Search Report and Written Opinion dated Feb. 18, 2011, Issued during proscution of Applicant's PCT/IL2010/000683.
Cryotherapy: A Novel Treatment Option for Prostate Cancer Article dated Aug. 12, 2008 from www.galilmedical.com.
Cancer's Molecular Sweet Tooth and the Warburg Effect, by Kim, Cancer Res 2006; 66: (18). Sep. 15, 2006.
Golden slingshot, The Economist, Nov. 6, 2008.
"Lipase-catalysed synthesis of glucose fatty acid esters in tert-butanol," by Degn, Biotechnology Letters 21: 275-280, 1999.
"Optimization of Carbohydrate Fatty Acid Ester Synthesis in Organic Media by a Lipase from Candida antarctica," by Degn, Biotechnology and Bioengineering, vol. 74, No. 6, Sep. 20, 2001.
Fluorodeoxyglucose, Wikipedia entry dated Jan. 18, 2009.
"Pathologic analysis of photothermal and photomechanical effects of laser-tissue interactions," by Thomsen, Photochem Photobiol. Jun. 1991;53(6):825-35.
Applied Thermal Engineering, Zalba et al., 23(3), Feb. 2003, pp. 251-283.
Fajardo et al. "Effects of Hyperthermia in a Malignant Tumor", Cancer 45: 613-623 (1980).
Short et al."Physical Hyperthermia and Cancer Therapy" Proceedings of the IEEE 68: 133-142 (1980)p. 136 col. 2 para 6.
Notice of Allowance dated Sep. 18, 2017, which issued during the prosecution of U.S. Appl. No. 15/478,849.
An Office Action dated Mar. 22, 2018, which issued during the prosecution of U.S. Appl. No. 15/852,293.
An International Search Report and a Written Opinion both dated Mar. 18, 2016, which issued during the prosecution of Applicant's PCT/IL2015/051146.
Minghui Zhang et al: "Encapsulated nano-heat-sinks for thermal management of heterogeneous chemical reactions", Nanoscale, vol. 2, No. 12, Jan. 1, 2010 (Jan. 1, 2010), pp. 2790-2797.
An Office Action dated May 16, 2016, which issued during the prosecution of U.S. Appl. No. 13/392,037.

* cited by examiner

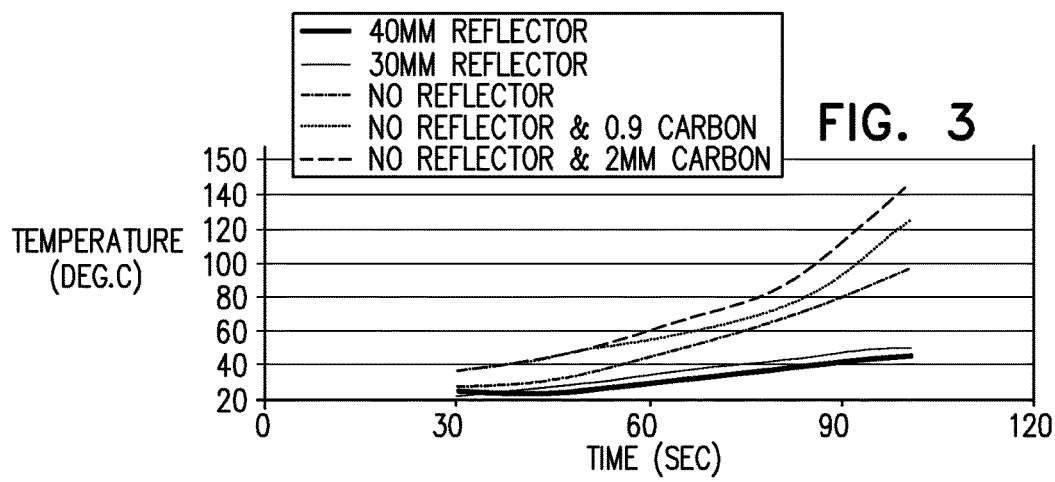
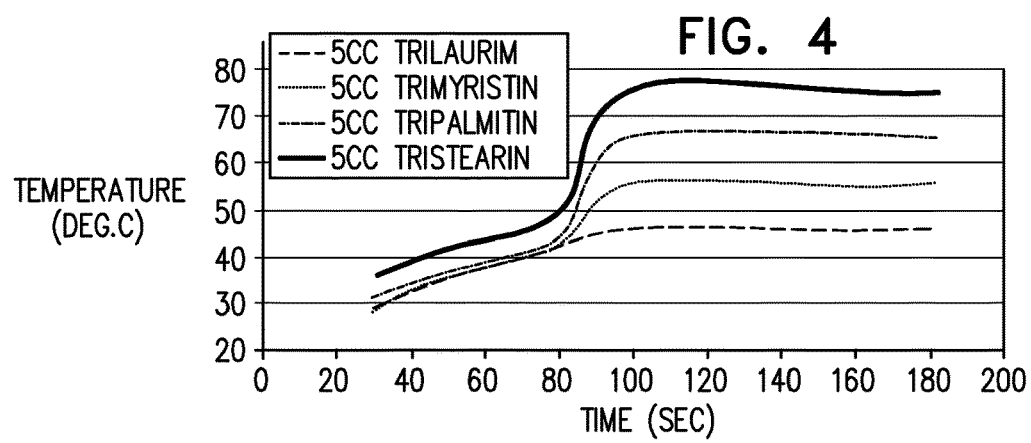
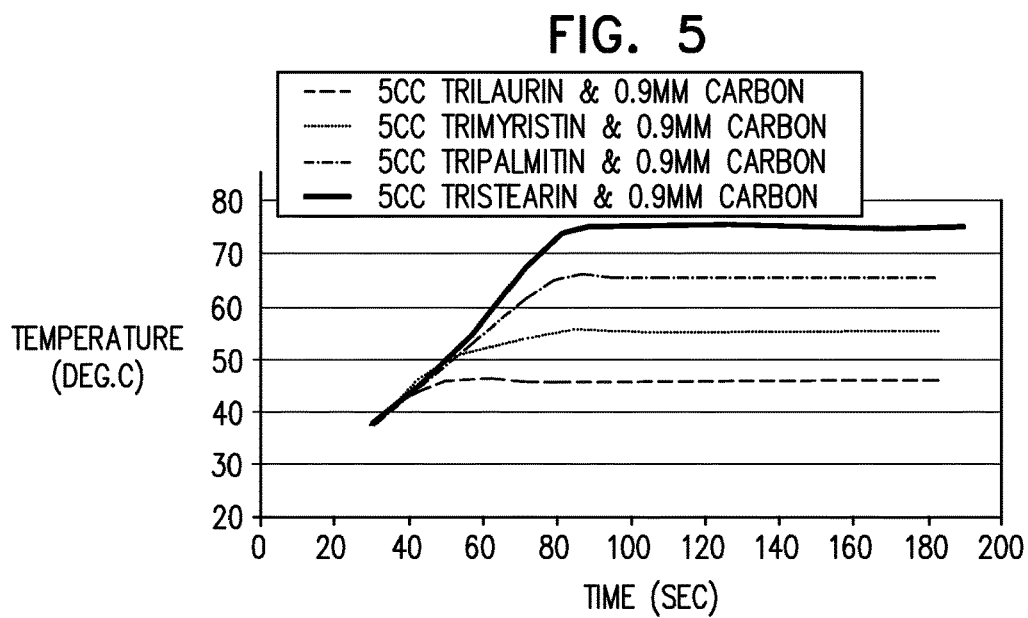

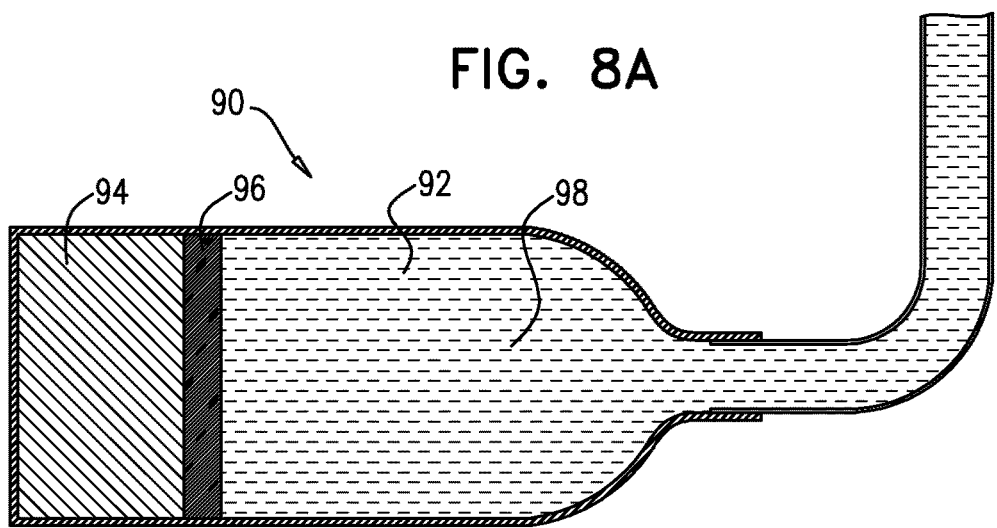
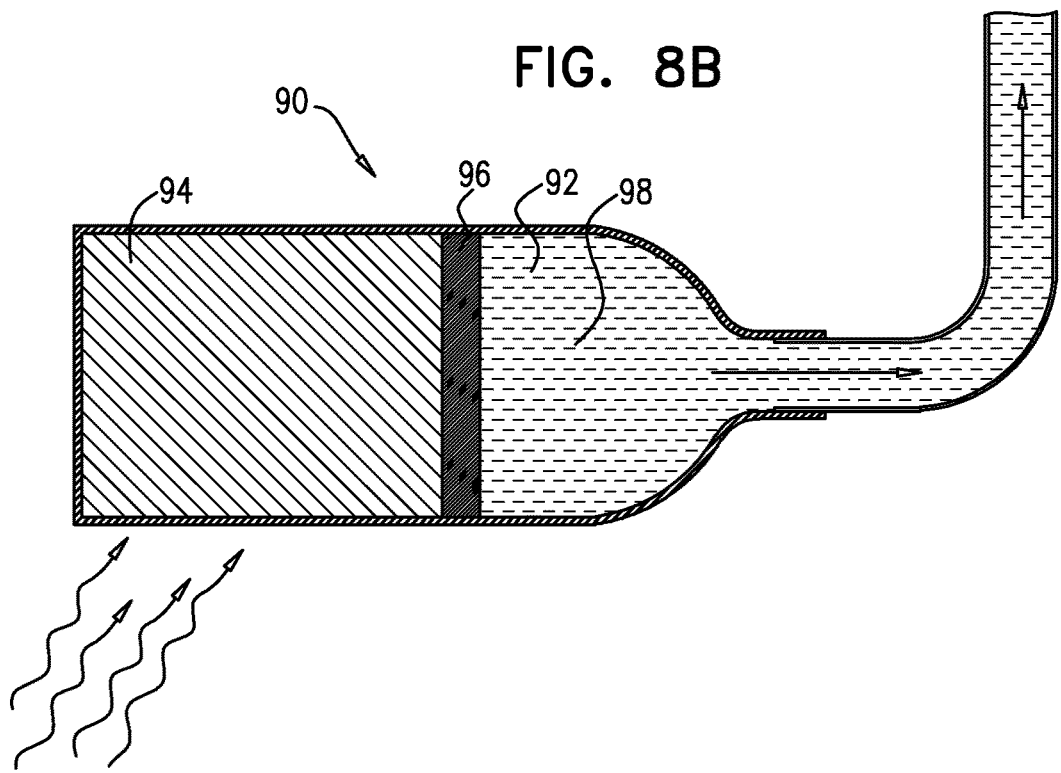

PHASE-CHANGE MATERIALS

CROSS REFERENCES TO RELATED APPLICATIONS

The present application is a continuation of U.S. Ser. No. 13/392,037 to Hof (published as US 2012/0221081; now U.S. Pat. No. 9,572,695), entitled "Phase-change and shape-change materials," which is a U.S. national phase of PCT Application no. PCT/IL2010/000683 to Hof (published as WO 11/024159), entitled "Phase-change and shape-change materials," filed Aug. 22, 2010, which claims priority from:

U.S. Provisional Patent Application 61/275,068, entitled "Phase change implant," to Hof, filed Aug. 24, 2009;

U.S. Provisional Patent Application 61/275,071, entitled "Shape and function change of implanted element," to Hof, filed Aug. 24, 2009;

U.S. Provisional Patent Application 61/275,089, entitled "Phase change materials for treating cancer," to Hof, filed Aug. 24, 2009.

All of the above-referenced applications are incorporated herein by reference.

FIELD OF EMBODIMENTS OF THE INVENTION

Some applications of the present invention generally relate to implanted medical apparatus. Specifically, some applications of the present invention relate to the use of phase-change and shape-change materials.

BACKGROUND

Stents are commonly placed inside blood vessels in order to widen narrowed or occluded blood vessels and, subsequently, to ensure that the blood vessel remains widened. Heating a stent subsequent to its implantation has been shown to prevent restenosis of the blood vessel (i.e., the re-narrowing of a blood vessel after it has been widened).

When a solid material is heated until its melting point, the material undergoes a phase-change to its liquid state. During the phase-change, the material accumulates a certain amount of heat, which is called the latent heat of fusion, or the enthalpy change of fusion. The temperature of the material stays relatively constant when the phase change occurs. When the process is reversed, i.e., when the material undergoes a phase-change from liquid to solid, the accumulated latent heat is released.

In oncology, the Warburg effect describes the observation that most cancer cells predominantly produce energy by glycolysis followed by lactic acid fermentation, rather than by oxidation of pyruvate like most healthy cells. The Warburg effect results in cancer cells consuming more than 20 times the quantity of glucose to produce energy than do healthy cells, ceteris paribus.

An article on Wikipedia (18 Jan. 2009) entitled "Fluorodeoxyglucose" states "FDG [Fluorodeoxyglucose] is most commonly used in the medical imaging modality positron emission tomography (PET): the fluorine in the FDG molecule is chosen to be the positron-emitting radioactive isotope fluorine-18, to produce 18F-FDG. After FDG is injected into a patient, a PET scanner can form images of the distribution of FDG around the body. The images can be assessed by a nuclear medicine physician or radiologist to provide diagnoses of various medical conditions . . . FDG, as a glucose analog, is taken up by high-glucose-using cells such as brain, kidney, and cancer cells, where phosphorylation prevents the glucose from being released intact. The 2-oxygen in glucose is needed for further glycolysis, so that (in common with 2-deoxy-D-glucose) FDG cannot be further metabolized in cells, and therefore the FDG-6-phosphate formed does not undergo glycolysis before radioactive decay. As a result, the distribution of 18F-FDG is a good reflection of the distribution of glucose uptake and phosphorylation by cells in the body."

A shape-memory alloy is an alloy, such as nitinol or copper-aluminum-nickel, that has a first shape when it is below a given temperature (the "transformation temperature"), and that changes to assume a second shape when it is heated to the transformation temperature.

PCT Publication WO 94/001165 to Gross describes a medication administering device includes a housing introducible into a body cavity and of a material insoluble in the body cavity fluids, but formed with an opening covered by a material which is soluble in body cavity fluids. A diaphragm divides the interior of the housing into a medication chamber including the opening, and a control chamber. An electrolytic cell in the control chamber generates a gas when electrical current is passed therethrough to deliver medication from the medication chamber through the opening into the body cavity at a rate controlled by the electrical current. The device can be in the form of a pill or capsule to be taken orally.

US Patent Application Publication 2006/0241747 to Shaoulian describes tissue shaping methods and devices. The devices are described as being adjusted within the body of a patient in a less invasive or non-invasive manner, such as by applying energy percutaneously or external to the patient's body. In one example, the device is positioned within the coronary sinus of the patient so as to effect changes in at least one dimension of the mitral valve annulus. The device is described as including a shape memory material that is responsive to changes in temperature and/or exposure to a magnetic field. In one example, the shape memory material is responsive to energy, such as electromagnetic or acoustic energy, applied from an energy source located outside the coronary sinus. A material having enhanced absorption characteristics with respect to the desired heating energy is also described as being used to facilitate heating and adjustment of the tissue shaping device.

U.S. Pat. No. 5,545,210 to Hess describes a permanent tissue supporting device, and a method for supporting tissue, wherein a stent-like member comprising a shape-memory alloy is permanently positioned to support the tissue of a tubular organ of a living body. The shape-memory alloy of the positioned stent-like member is in the martensitic state and exhibits a strain on a horizontal plateau of a stress-strain curve of the shape-memory alloy when permanently positioned in the tubular organ.

U.S. Pat. No. 6,059,810 to Brown describes a stent for reinforcing a vessel wall, the stent being expandable and comprised of a shape memory alloy which in the normal implanted condition is in the martensitic phase at body temperature, the stent further having a larger parent or austenitic shape and diameter when heated above its transition temperature.

Galil Medical (Yokneam, Israel) manufactures cryotherapy systems.

The following references may be of interest:
U.S. Pat. No. 6,805,711 to Quijano
U.S. Pat. No. 6,451,044 to Naghavi et al.
U.S. Pat. No. 6,323,459 to Maynard
U.S. Pat. No. 6,120,534 to Ruiz U.S. Pat. No. 5,964,744 to Balbierz
U.S. Pat. No. 5,830,179 to Mikus
U.S. Pat. No. 5,716,410 to Wang
U.S. Pat. No. 5,667,522 to Flomenblit
US Patent Application Publication 2002/0183829 to Doscher et al.
US Patent Application Publication 2004/0253304 to Gross
US Patent Application Publication 2004/0180086 to Ramtoola
United States Patent Application Publication 2005/0055082 to Ben Muvhar
US Patent Application Publication 2005/0288777 to Rhee
US Patent Application Publication 2006/0074479 to Bailey
US Patent Application Publication 2006/0241747 to Shaoulian et al.
US Patent Application Publication 2008/021537 to Ben Muvhar
PCT Publication WO 02/000145 to Diamantopoulos
PCT Publication WO 03/028522 to Ben Muvhar
"Pathologic analysis of photothermal and photomechanical effects of laser-tissue interactions," by Thomsen, Photochem Photobiol. 1991 June; 53(6):825-35
"The next generation of cancer treatments may be delivered by nanoparticles," The Economist, Nov. 6, 2008
"Lipase-catalysed synthesis of glucose fatty acid esters in tert-butanol," by Degn et al., Biotechnology Letters 21: 275-280, 1999
"Optimization of Carbohydrate Fatty Acid Ester Synthesis in Organic Media by a Lipase from *Candida Antarctica*," by Degn et al., Biotechnology and Bioengineering, Vol. 74, No. 6, Sep. 20, 2001
"Cancer's Molecular Sweet Tooth and the Warburg Effect," by Kim et al., Cancer Res 2006; 66: (18). Sep. 15, 2006
Applied Thermal Engineering, Zalba et al., 23(3), February 2003, pp. 251-283

SUMMARY OF THE INVENTION

For some applications of the invention, an element (e.g., a stent) is implanted within a subject's body. A phase-change material is implanted within the subject's body in a vicinity of the element. The phase-change material absorbs heat from the element by being heated to its phase-change temperature. Typically, in response to being heated, the phase-change material absorbs latent heat of fusion, but not all of the phase-change material undergoes a change in phase. For some applications, at least a portion of the phase-change material undergoes a change in phase (for example, from solid to liquid, or solid to gel).

For some applications, the element is a stent that is implanted inside a blood vessel. When the stent is heated to prevent restenosis of the blood vessel, the phase-change material prevents the stent, and/or tissue surrounding the stent, from overheating, by absorbing heat from the stent. For some applications, the phase-change material absorbs heat from an implanted element during procedures during which the implanted element may otherwise overheat. For example, the phase-change material may absorb heat from a stent that is implanted inside a subject while the subject undergoes an MRI procedure, or another procedure during which the stent is exposed to electromagnetic fields.

For some applications, a portion of a subject's body is heated, for example, during a medical procedure. A phase-change material is placed within the subject's body in a vicinity of the heated portion. The phase-change material absorbs heat from the vicinity of the heated portion.

For some applications, a portion of the subject's body is cooled, for example, a portion of the subject's body is cryoablated (e.g., using a cryoablation system manufactured by Galil Medical). A phase-change material is implanted in tissue surrounding the portion. The phase-change material releases latent heat energy by being cooled to its phase change temperature (e.g., the transition temperature from liquid to solid, or from gel to solid), thereby preventing damage to the surrounding tissue.

For some applications of the present invention, a system is provided for rupturing cancer cells of a subject, the subject having cancer cells and healthy cells. Clusters of phase-change molecules are coupled to respective first molecules (e.g., respective molecules of glucose). A plurality of the first molecules are administered to the subject and couple to the cancer cells to a greater extent than to the healthy cells. Typically, the first molecule is selected such that, by virtue of the Warburg effect, the first molecule couples to the cancer cells to a greater extent than to the healthy cells. For example, respective first molecules may be glucose molecules, and more than twenty times as many glucose molecules may become coupled to the cancer cells as become coupled to the healthy cells.

While the first molecules are coupled to the cancer cells, energy is transmitted toward the clusters of phase-change molecules. In response to the energy striking the clusters of phase-change molecules, the temperature of the region in which the phase-change molecules are disposed rises, but does not rise above the phase-change temperature of the phase-change molecules. This is because, at the phase-change temperature, the heat that is transmitted toward the region is absorbed by the phase-change molecules as latent heat. The heating of the phase-change molecules typically heats the cancer cells, thereby killing the cancer cells. In some circumstances, the absorption of the energy by the phase-change molecules causes the phase-change molecules to vibrate, thereby rupturing the membranes of the cancer cells. For some applications, energy is transmitted toward the clusters at the resonance frequency of the phase-change molecules, in order to enhance the absorption of energy by the phase-change molecules.

For some applications of the present invention, an implantable element is implanted inside a subject's body. The element includes a shape-memory material having a transformation temperature. The implantable element performs a first therapeutic function with respect to a portion of the subject's body when the shape-memory material is in a first shape. An energy applicator changes the shape-memory material from the first shape to a second shape, by raising a temperature of the shape-memory material to the transformation temperature of the shape-memory material. When the shape-memory material is in the second shape, the implantable element performs a second therapeutic function with respect to the portion, the second therapeutic function being qualitatively different from the first therapeutic function.

For some applications, the implantable element comprises a stent. The stent is implanted into a blood vessel of the subject, which is typically a narrowed blood vessel. While the stent is in a first configuration, it opens the blood vessel by supporting the inner walls of the blood vessel. Subsequently, the stent is heated and the shape of the stent changes to the shape of a venturi tube. The venturi-tube shaped stent causes the generation of new blood vessels in the vicinity of the blood vessel in which the stent is disposed, as described hereinbelow, and/or in accordance with the techniques described in PCT Publication WO 03/028522 to Ben Muvhar, which is incorporated herein by reference.

There is therefore provided, in accordance with some applications of the present invention, apparatus, including:
an implantable element configured to be implanted within a body of a subject; and
a phase-change material configured:
to be implanted within the subject's body in a vicinity of the element, and
to absorb heat from the element by absorbing latent heat of fusion resulting from a phase-change of the phase-change material selected from the group consisting of: wax to liquid, solid to liquid, solid to gel, and gel to liquid, in response to the element being heated.

For some applications, less than all of the phase-change material is configured to undergo the selected phase change, in response to the element being heated.

For some applications, the phase-change material includes paraffin.

For some applications, the phase-change material includes an organic phase-change material.

For some applications, the implantable element includes a stent.

For some applications, the phase-change material is configured to absorb heat from the element in response to the element being heated by being exposed to an electromagnetic field.

For some applications, the phase-change material has a phase-change temperature of 4.5 C to 145 C.

For some applications, the phase-change material has a phase-change temperature of 45 C to 60 C.

For some applications, the phase-change material has a phase-change temperature of 60 C to 80 C.

For some applications, the phase-change material is configured to be implanted in a separate implantation step from implantation of the implantable element.

For some applications, the phase-change material is configured not to be attached to the implantable element when the implantable element and the phase-change material are implanted within the subject's body.

For some applications, the phase-change material and the implantable element are configured to be implanted in a single implantation step.

For some applications, the phase-change material includes a coating that coats the implantable element.

For some applications, the phase-change material is disposed within the implantable element.

For some applications, the implantable element defines a hollow volume, and the phase-change material is disposed inside the hollow volume.

There is further provided, in accordance with some applications of the present invention, a method, including:
placing a phase-change material within a body of a subject; and
causing the phase-change material within the subject's body to absorb latent heat of fusion resulting from a phase-change of the phase-change material selected from the group consisting of: wax to liquid, solid to liquid, solid to gel, and gel to liquid, by heating the phase-change material.

For some applications, causing the phase-change material to absorb the latent heat of fusion includes causing less than all of the phase-change material to undergo the selected phase change, by heating the phase-change material.

For some applications, causing the phase-change material to absorb the latent heat of fusion includes causing the phase-change material to absorb heat from a portion of the subject's body in a vicinity of the phase-change material.

There is further provided, in accordance with some applications of the present invention, apparatus, including:
a heating device configured to heat a portion of a body of a subject; and
a phase-change material configured:
to be placed within the subject's body in a vicinity of the portion, and
to absorb heat from the vicinity of the portion by absorbing latent heat of fusion resulting from a phase-change of the phase-change material selected from the group consisting of: wax to liquid, solid to liquid, solid to gel, and gel to liquid, in response to the portion of the subject's body being heated.

For some applications, less than all of the phase-change material is configured to undergo the selected phase change, in response to the portion being heated.

For some applications, the phase-change material includes paraffin.

For some applications, the phase-change material includes an organic phase-change material.

For some applications, the phase-change material includes a gel configured to be injected into the subject's body in the vicinity of the portion.

For some applications, the phase-change material includes a solid pellet configured to be injected into the subject's body in the vicinity of the portion.

For some applications, the phase-change material has a phase-change temperature of 4.5 C to 145 C.

For some applications, the phase-change material has a phase-change temperature of 45 C to 60 C.

For some applications, the phase-change material has a phase-change temperature of 60 C to 80 C.

For some applications, the apparatus further includes an energy absorbing element configured to be implanted within the portion and to absorb energy from the heating device.

For some applications, the energy absorbing element includes a carbon cylinder having a diameter that is at least 0.9 mm.

For some applications, the energy absorbing element includes a biocompatible metal.

There is further provided, in accordance with some applications of the present invention, apparatus, including:
an implantable element configured to be implanted within a body of a subject; and
a phase-change material configured:
to be implanted within the subject's body in a vicinity of the element, and
to release latent heat of fusion resulting from a phase-change of the phase-change material selected from the group consisting of: liquid to wax, liquid to solid, gel to solid, and liquid to gel, in response to the element being cooled.

There is additionally provided, in accordance with some applications of the present invention, a method, including:
placing a phase-change material within a body of a subject; and
causing the phase-change material within the subject's body to release latent heat of fusion resulting from a phase-change of the phase-change material selected from the group consisting of: liquid to wax, liquid to solid, gel to solid, and liquid to gel, by cooling the phase-change material.

There is further provided, in accordance with some applications of the present invention, apparatus for killing cancer cells of a subject, the subject having cancer cells and healthy cells, the apparatus including:

a plurality of first molecules configured to be coupled to the cancer cells to a greater extent than to the healthy cells, in response to being administered to the subject;

a plurality of clusters of phase-change molecules, each of the clusters coupled to a respective one of the first molecules; and an energy transmission unit, configured to kill cancer cells coupled to the first molecules by heating the cancer cells, by transmitting energy toward the clusters that selectively heats the clusters.

For some applications, the energy transmission unit is configured to rupture membranes of the cancer cells by heating the cancer cells.

For some applications, the energy transmission unit is configured to heat the clusters to a melting temperature of the phase-change molecules, and the phase-change molecules are configured to absorb latent heat of fusion in response to the clusters being heated.

For some applications, the energy transmission unit is configured to transmit energy at a resonance frequency of the phase-change molecules.

For some applications, the phase-change molecules include paraffin molecules.

For some applications, the phase-change molecules include organic phase-change molecules.

For some applications, the energy transmission unit is configured to heat the clusters such that less than all of the phase-change molecules in each of the clusters undergo the selected phase change, in response to the clusters being heated.

For some applications, the first molecules include glucose molecules.

For some applications, the clusters of phase-change molecules have a phase-change temperature between 60 and 80 C.

For some applications, the clusters of phase-change molecules have a phase-change temperature between 45 and 60 C.

For some applications, the energy transmission unit is configured to heat the clusters such that a temperature of the clusters does not rise above a phase-change temperature of the phase-change molecules, in response to the clusters being heated.

For some applications, the energy transmission unit is configured to discontinue the transmission of the energy in response to an indication of the temperature of the clusters.

For some applications, the energy transmission unit is configured to sense a temperature of the clusters and to discontinue the transmission of the energy in response to the sensed temperature.

For some applications, the energy transmission unit is configured to discontinue transmission of the energy in response to a duration of transmission of the energy.

There is further provided, in accordance with some applications of the present invention, a method for killing cancer cells of a subject, the subject having the cancer cells and healthy cells, the method including:

administering to the subject a plurality of first molecules, each of the first molecules having a cluster of phase-change molecules coupled thereto, the first molecules being configured to be coupled to the cancer cells to a greater extent than to the healthy cells; and killing the cancer cells by heating the cancer cells, by transmitting energy toward the clusters that selectively heats the clusters.

For some applications, transmitting energy toward the clusters includes irradiating multiple sites to which the cancer cells may have metastasized.

For some applications, the method further includes imaging the subject while transmitting energy toward the clusters.

For some applications, imaging the subject includes imaging the cancer cells using a heat-sensitive imaging protocol.

There is therefore provided, in accordance with some applications of the present invention, apparatus for use with a portion of a body of a subject, including:

an implantable element, including a shape-memory material having a transformation temperature, the implantable element configured to be implanted in the portion, and to perform a first therapeutic function with respect to the portion when the shape-memory material is in a first shape, and while the implantable element is implanted in the portion; and an energy applicator, configured to change the shape-memory material from the first shape to a second shape, by raising a temperature of the shape-memory material to the transformation temperature, the implantable element being configured to perform a second therapeutic function with respect to the portion when the shape-memory material is in the second shape, while the implantable element is implanted in the portion, the second therapeutic function being qualitatively different from the first therapeutic function.

For some applications, the implantable element is shaped as a cylindrical stent when the shape-memory material is in the first shape.

For some applications, the implantable element is shaped as a venturi tube when the shape-memory material is in the second shape.

There is further provided, in accordance with some applications of the present invention, a method for use with a portion of a body of a subject, including:

implanting an implantable element in the portion;

performing a first therapeutic function with respect to the portion using the implantable element while the implantable element is implanted in the portion, the implantable element including a shape-memory material that has a transformation temperature, the shape-memory material being in a first shape during the performing of the first therapeutic function;

changing the shape-memory material from the first shape to a second shape by raising a temperature of the shape-memory material to the transformation temperature; and performing a second therapeutic function with respect to the portion using the implantable element, while the implantable element is implanted in the portion, and when the shape-memory material is in the second shape.

For some applications, performing the first therapeutic function includes opening a blood vessel of the subject, the implantable element being shaped as a cylindrical stent when the shape-memory material is in the first shape thereof.

For some applications, performing the second therapeutic function includes increasing blood pressure in a portion of the blood vessel that is proximal to the implantable element, the implantable element being shaped as a venturi tube when the shape-memory material is in the second shape thereof.

There is additionally provided, in accordance with some applications of the present invention, a method for use with a portion of a body of a subject, including:

implanting an implantable element in the portion;

performing a first therapeutic function with respect to the portion using the implantable element, while the implantable element is implanted in the portion, the implantable element being in a first mechanical configuration during the performing of the first therapeutic function;

changing the implantable element from the first mechanical configuration to a second mechanical configuration by raising a temperature of the implantable element; and performing a second therapeutic function with respect to the portion using the implantable element, while the implantable element is implanted in the portion, and when the implantable element material is in the second mechanical configuration.

There is further provided, in accordance with some applications of the present invention, an implantable pump for dispensing a drug, including:

a drug chamber configured to contain a drug; and a shape-memory material configured to force at least some of the drug out of the pump, by expanding, by being heated to a given temperature.

For some applications, the shape-change material is configured to expand by being heated to a temperature of 40-60 C.

For some applications, the drug includes a chemotherapy agent, and the drug chamber is configured to contain the chemotherapy agent.

There is additionally provided, in accordance with some applications of the present invention, a method, including:

implanting a drug pump inside a body of a subject, the pump including a drug chamber that is configured to contain a drug; and forcing at least a portion of the drug out of the drug chamber by expanding a shape-memory material that has a transformation temperature, by heating the shape-memory material to the transformation temperature for a first given time period.

For some applications, the method further includes forcing a further portion of the drug out of the drug chamber by further expanding the shape-memory material by heating the shape-memory material to the transformation temperature for a second given time period.

For some applications, heating the shape-memory material to the transformation temperature includes heating the shape-memory material to a temperature of 40-60 C.

For some applications, the medication includes a chemotherapy agent, and forcing the medication out of the drug chamber includes forcing the chemotherapy agent out of the drug chamber.

The present invention will be more fully understood from the following detailed description of embodiments thereof, taken together with the drawings, in which:

BRIEF DESCRIPTION OF THE DRAWINGS

FIG. 3 is a graph showing experimental results of five pieces of tissue that were heated in a control experiment;

FIG. 4 is a graph showing experimental results of four pieces of tissue that were injected with phase-change materials and were heated, in accordance with some applications of the present invention;

FIG. 5 is a graph showing further experimental results of four pieces of tissue that were injected with phase-change materials and were heated, in accordance with some applications of the present invention.

FIGS. 8A-B are schematic illustrations of a portion of a drug pump having an expansible shape-memory portion, in accordance with some applications of the present invention.

DETAILED DESCRIPTION OF EMBODIMENTS

Figure 1A:
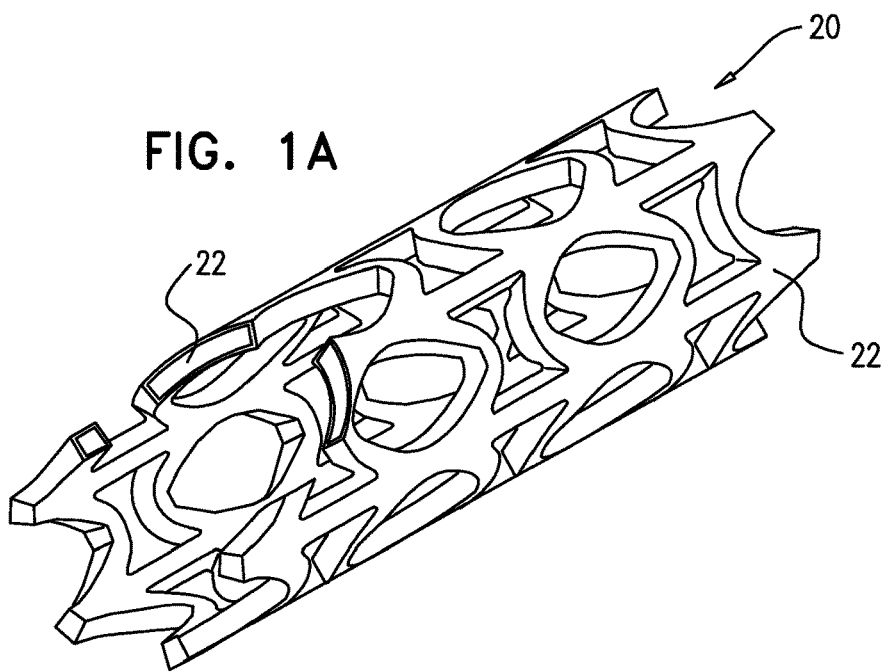
FIG. 1A is a schematic illustration of a phase-change material inside a hollow implantable element, in accordance with some applications of the present invention.

Reference is now made to FIG. 1A, which is a schematic illustration of a phase-change material 22 inside an implantable element 20, in accordance with some applications of the present invention. The phase-change material absorbs heat from the element by being heated to the phase-change temperature of the phase-change material and absorbing latent heat energy.

For some applications, implantable element 20 is a stent, and phase-change material 22 is disposed inside the stent. For example, the stent may be shaped as a hollow tube, or may be shaped in a different shape that allows the stent to contain the phase-change material therein. Alternatively or additionally, the phase-change material coats the implantable element. Typically, for applications in which the phase-change material is inside the implantable element, and/or coats the implantable element, phase-change material 22 and implantable element 20 are implanted within a subject's body in a single implantation step. For some applications, the phase-change material is not attached to the implantable element when the phase-change material and the implantable element are within the subject's body. For example, the phase-change material may be implanted in tissue that is at a distance of several millimeters or micrometers from the implantable element, and the phase-change material may reduce heating of the tissue when the implantable element is heated. For some applications, the phase-change material is implanted in a separate implantation step from the implantation of the implantable element.

For some applications, one or more of the phase-change materials that appear (hereinbelow) in Table 1 and/or in Table 2 are used as phase-change material 22. Typically, a phase-change material is selected as the phase-change material, on the basis of the phase-change temperature of the phase-change material. For example, if it is desired to heat implantable element 20 to a temperature of 42 C, paraffin having a molecule length of 16 carbon atoms (C16) may be selected, in accordance with the data in Table 1 (which is extracted from Zalba et al., Applied Thermal Engineering, 23(3), February 2003, pp. 251-283). When the element is heated to 42 C, the selected phase-change material absorbs energy as it absorbs latent heat of fusion. While the phase-change material absorbs energy, the heating of the element and/or the surrounding tissue is inhibited. For some applications, other melting temperatures and corresponding materials are used.

TABLE 1

Melting temperatures of paraffin molecules

| Compound | Melting temperature (° C.) | Heat of fusion $\left(\frac{Kj}{Kg}\right)$ |
|---|---|---|
| Paraffin C16-C28 | 42-44 | 189 |
| Paraffin C20-C33 | 48-50 | 189 |
| Paraffin C22-C45 | 58-60 | 189 |
| Paraffin wax | 64 | 173.6 |
| Paraffin C28-C50 | 66-68 | 189 |
| Paraffin RT40 | 43 | 181 |
| Paraffin RT50 | 54 | 195 |
| Paraffin RT65 | 64 | 207 |
| Paraffin RT80 | 79 | 209 |
| Paraffin RT90 | 90 | 197 |
| Paraffin RT110 | 112 | 213 |

TABLE 2

Melting temperature of organic phase-change materials:

| Compound | Melting Temperature (° C.) | Heat of fusion $\left(\frac{Kj}{Kg}\right)$ |
|---|---|---|
| Paraffin C14 | 4.5 | 165 |
| Paraffin C15-C16 | 8 | 153 |
| Polyglycol E400 | 8 | 99.6 |
| Dimethyl-sulfoxide (DMS) | 16.5 | 85.7 |
| Paraffin C16-C18 | 20-22 | 152 |
| Polyglycol E600 | 22 | 189 |
| Paraffin C13-C24 | 22-24 | 189 |
| 1-Dodecanol | 26 | 200 |
| Paraffin C18 | 28 | 244 |
| 1-Tetradecanol | 26 | 200 |
| Paraffin C16-C28 | 42-44 | 189 |
| Paraffin C20-C33 | 48-50 | 189 |
| Paraffin C22-C45 | 58-60 | 189 |
| Paraffin Wax | 64 | 173.6 |
| Polyglycol E6000 | 66 | 190 |
| Paraffin C28-C30 | 66-68 | 189 |
| Biphenyl | 71 | 119.2 |
| Propionamide | 79 | 168.2 |
| Naphthalene | 80 | 147.7 |
| Erythritol | 118 | 339.8 |
| HDPE | 100-150 | 200 |
| Trans-1,4-polybutadiene (TPB) | 145 | 144 |

For some applications, one or more of the following organic phase-change materials is used for phase-change material 22: crude oil, paraffin produced by the Fischer-Tropsch process, and an organic material having saturated, unsaturated, straight, or branched carbon chain molecules. The phase-change material may include, for example, trilaurin, trimyristin, tripalmitin, tristearin, and/or any suitable type of paraffin or paraffin wax.

The phase-change temperature (e.g., the melting temperature) of the phase-change material is typically 4.5 C to 145 C, e.g., 45 C to 60 C, or 60 C to 80 C. For some applications, the phase-change material has relatively low thermal conductivity, and is arranged to have a large surface area to overcome the low thermal conductivity and increase the flow of heat into the phase-change material.

For some applications, when coupling phase-change material 22 to implantable element 20, and/or when implanting the phase-change material, it is assumed that the phase-change material will undergo thermal expansion, and the coupling and/or implantation is performed accordingly. For example, if the phase-change material is disposed inside a hollow volume inside a stent (as shown in FIG. 1A), 10 percent of the hollow volume may be left empty to allow for the thermal expansion of the phase-change material inside the hollow volume. Alternatively, the phase-change material is disposed inside a hollow volume inside a stent (as shown in FIG. 1A), and the stent is hermetically sealed, in order to reduce or prevent expansion of the phase-change material.

Figure 1B:
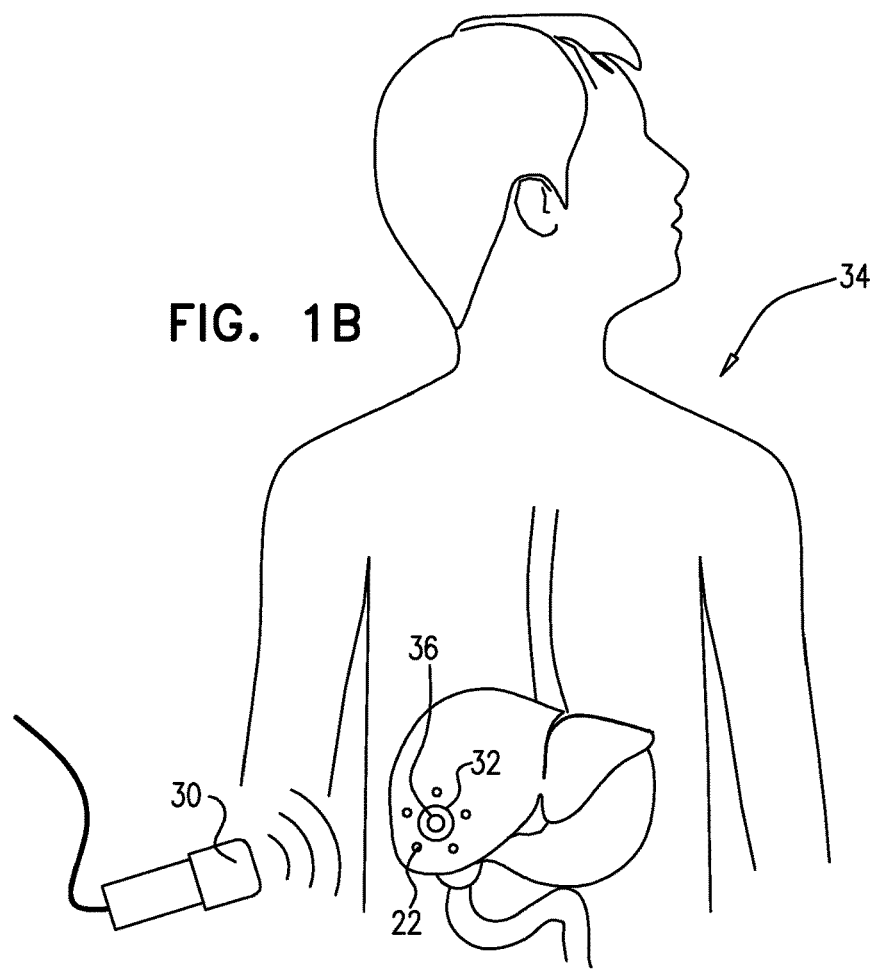
FIG. 1B is a schematic illustration of a phase-change material implanted in a vicinity of a portion of a subject's body that is being heated, in accordance with some applications of the present invention.

Reference is now made to FIG. 1B, which is a schematic illustration of phase-change material 22 implanted in a vicinity of a portion 32 of a subject's body 34 that is being heated by a heating device 30 (e.g., an ultrasound transducer), in accordance with some applications of the present invention. For some applications, the phase-change material is placed within the subject's body in the vicinity of portion 32. During the heating of portion 32, the phase-change material absorbs latent heat of fusion from tissue in the vicinity of the portion by being heated to the phase-change temperature of the phase-change material. Typically, one of the phase-change materials that appears in Table 1, or another phase-change material is selected, based upon the temperature to which portion 32 is heated.

For some applications, portion 32 includes cancerous tissue which is heated by heating device 30 to denature the tissue. The absorption of heat near other tissue in the vicinity of portion 32 prevents the other tissue from overheating and becoming denatured. For some applications, the temperature to which portion 32 is heated depends on the nature of portion 32. For example, denaturing tissue of the kidney, which has a high level of perfusion, requires heating the tissue to a higher temperature than would be required in order to denature tissue of the lungs.

For some applications, phase-change material 22 is injected into tissue in the vicinity of portion 32, and/or in the vicinity of implantable element 20, in the form of pellets and/or gel.

For some applications, an energy absorbing element 36, such as carbon or graphite, is inserted into portion 32 to facilitate the heating of the tissue by efficiently absorbing energy from heating device 30 and undergoing an elevation in temperature.

For some applications, implantable element 20 is coupled to phase-change material 22, as described hereinabove. The implantable element and the phase-change material are implanted in the vicinity of portion 32. Heating device 30 heats the implantable element, and, simultaneously, the phase-change material prevents the temperature of the implantable element from rising above a given temperature. For some applications, implanting the implantable element at a specific implantation site with respect to portion 32 facilitates the directing of the heat toward the portion.

Figure 2A:
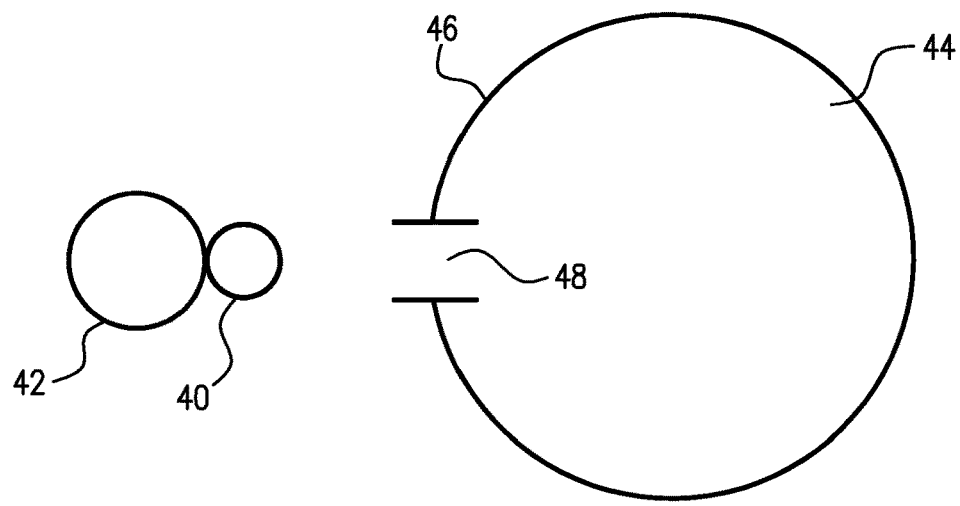
FIG. 2A is a schematic illustration of a cluster of phase-change molecules coupled to a glucose molecule, near a cancer cell, in accordance with some applications of the present invention.

Reference is now made to FIG. 2A, which is a schematic illustration of a cancer-treatment substance that includes a sugar molecule, e.g., a glucose molecule 40, coupled to a cluster 42 of phase-change molecules, in accordance with some applications of the present invention. The substance is administered to the subject, for example, orally, or by injection. The substance is configured such that cancer cells 44 absorb more of the substance than healthy cells of the surrounding tissue, due to the preferential uptake of the glucose molecules by the cancer cells. The preferential uptake of glucose molecules by cancer cells is based on the Warburg effect, described hereinabove in the Background, and as described in "Cancer's Molecular Sweet Tooth and the Warburg Effect," by Kim et al., Cancer Res 2006; 66:

(18). Sep. 15, 2006, which is incorporated herein by reference. (The principle of cancer cells preferentially uptaking glucose molecules forms the basis of certain PET-CT imaging protocols, as described in the Wikipedia article entitled "Fluorodeoxyglucose," which is incorporated herein by reference.)

For some applications, techniques that are known in the art are used for coupling the phase-change molecules to glucose molecule 40. For example, techniques may be used that are based on techniques described in the following articles, which are incorporated herein by reference: (a) "Lipase-catalysed synthesis of glucose fatty acid esters in tert-butanol," by Degn et al., Biotechnology Letters 21: 275-280, 1999, and (b) "Optimization of Carbohydrate Fatty Acid Ester Synthesis in Organic Media by a Lipase from Candida Antarctica," by Degn et al., Biotechnology and Bioengineering, Vol. 74, No. 6, Sep. 20, 2001.

Figure 2B:
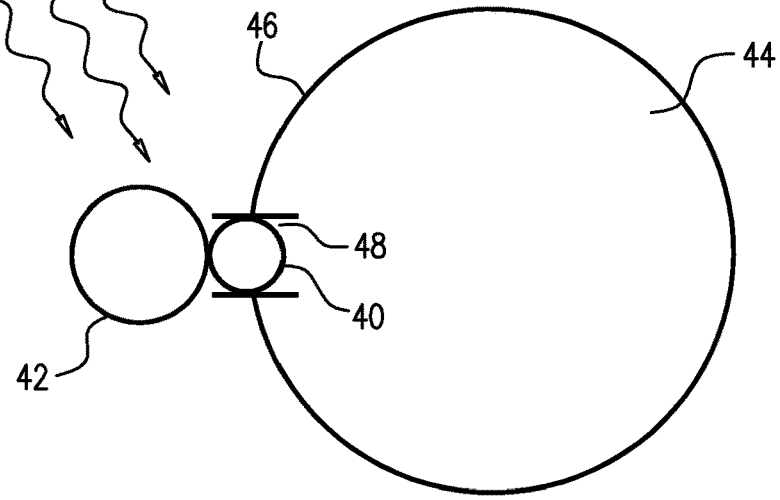
FIG. 2B is a schematic illustration of the cluster of phase-change molecules coupled to the membrane of a cancer cell via the glucose molecule, in accordance with some applications of the present invention.

Reference is now made to FIG. 2B, which is a schematic illustration of cluster 42 of phase-change molecules coupled to membrane 46 of cancer cell 44, via glucose molecule 40, in accordance with some applications of the present invention. Typically, glucose molecule 40 passes at least partially through membrane 46 of cancer cell 44, via a glucose channel 48. Further typically, the cluster of phase-change molecules is unable to pass through the cell membrane, but since it remains coupled to the glucose molecule, it becomes coupled to the cell membrane. (Although, FIG. 2B shows that phase-change molecule 42 is unable to pass through glucose channel 48 due to the size of cluster 42 of phase-change molecules, the scope of the present invention includes using a cluster of phase-change molecules that is unable to pass through the glucose channel for another reason.)

While cluster 42 of phase-change molecules is coupled to membrane 46, energy is directed toward cancer cell 44. For example, an energy transmission unit 50 irradiates a region of the body in which cancer cell 44 is located. For some applications, the cancer cell is heated to the phase-change temperature of the phase-change molecules. For some applications, the phase-change molecules absorb heat without all of the molecules changing phase (e.g., from solid to liquid), the heat being absorbed as latent heat of fusion of the phase change. Typically, the temperature of the phase-change molecules and the vicinity of the phase-change molecules remains substantially constant once the phase-change molecules have been heated to the phase-change temperature. Further typically, the energy transmission unit does not heat the cluster to a temperature that is greater than the phase-change temperature. For some applications, the energy transmission unit discontinues the transmission of energy in response to an indication of the temperature of the clusters. For example, the energy transmission unit may sense a temperature of the clusters using known techniques, and discontinue the transmission of the energy in response to the sensed temperature. Alternatively or additionally, the energy transmission unit discontinues transmission of the energy in response to a duration of transmission of the energy, i.e., the unit ceases to transmit energy after a given time period.

Typically, the heating of the phase-change molecules heats the cancer cell, thereby killing the cancer cell. For some applications, the cancer cell is irradiated at a frequency that is the resonance frequency of the phase-change molecule. For some applications, the heating of cluster 42 causes the cluster to vibrate. The vibration of cluster 42, while the cluster is coupled to cell membrane 46, causes the cancer cell membrane to rupture, thereby killing the cancer cell.

For some applications, the effect of the heating of the phase-change molecules on the cancer is in accordance with Table 3, which appears in an article by Thomsen, entitled "Pathologic analysis of photothermal and photomechanical effects of laser-tissue interactions" (*Photochem Photobiol.* 1991 June; 53(6):825-35), which is incorporated herein by reference:

TABLE 3

Histopathological effect of heating on cells

| Thermal damage mechanism | Temperature of onset: range (° C.) | Heating times | Histopathology effect |
|---|---|---|---|
| Low-temperature damage accumulation processes | 40-45 | Hours | Reversible cell injury: heat inactivation of enzymes; metabolic acceleration |
| | Low 40+ | Hours to minutes | Edema and hyperemia |
| | 43-45+ | Hours | Cell death: deactivation of enzymes |
| | Unknown | Unknown | Cell shrinkage and hyperchromasia |
| | 43+ | Minutes | Birefringence loss in frozen and thawed myocardium |
| | 45+ | Minutes to seconds | Thermal denaturization of structural proteins in fresh tissue |
| | Unknown | Unknown | Cell membrane rupture |
| | 50-90 | Minutes to seconds | Hyalinization of collagen |
| | 54-78 | 3.6 to 0.4 seconds | Birefringence loss in laser irradiated fresh myocardium |
| | 55-95+ | Minutes | Birefringence changes in collagen |
| Water dominated processes | 100± | Seconds | Extracellular vacuole formation. Rupture of vacuoles, "popcorn" effect |
| | 100-200 | Seconds to milliseconds | Tissue ablation by explosive fragmentation |
| | Over 200 | Seconds to picoseconds | Tissue ablation |

Typically, as stated hereinabove, the region of the subject's body in which cancer cells 44 are located is heated to the phase-change temperature of the phase-change molecules. For some applications, phase-change molecules having a phase-change temperature of 45 C to 60 C, or 60 C to 80 C are used in cluster 42. Further typically, during the heating, the healthy cells do not absorb as much heat as the phase-change molecules, because the radiation is selected to be at the resonance frequency of the phase-change material molecules, which are predominantly in contact with or very near to cancer cells.

For some applications, when it is suspected that cancer tissue has metastasized, the cancer-treatment substance is administered to the subject. Energy is then directed toward regions of the subject's body to which the cancer may have metastasized. If cancer cells are present in the region, the phase-change material molecules preferentially absorb the energy, and the cancer cells are killed, while the healthy cells remain generally intact. (Use of these applications may include killing some healthy cells, along with killing a large number of cancer cells.) For some applications, when it is suspected that cancer tissue has metastasized, the subject's whole body is irradiated with the energy that is preferentially absorbed by the clusters, subsequent to administering the substance to the subject. As described hereinabove, due the coupling of the phase-change molecules to the cancer cells, the cancer cells are selectively heated and are killed.

For some applications, the methods described herein are applied to the subject while imaging the subject, for example, using CT and/or MRI imaging protocols. For some applications, the substance is administered to the subject, and the subject's body (or a region thereof) is irradiated with the energy that is preferentially absorbed by the clusters, as described herein. While the subject's body is irradiated, the subject's body is imaged using a heat-sensitive imaging protocol (for example, using MRI) to detect which regions of the subject's body (including cancer cells) have been heated.

In accordance with respective applications of the invention, selection criteria for selecting phase-change molecules for use in cluster 42 include thermodynamic, kinetic, and chemical properties of the phase-change molecules. For some applications, the phase-change molecules are selected to have given thermodynamic properties, such as a melting temperature in the desired operating temperature range, a high latent heat of fusion per unit volume, high specific heat, high density, high thermal conductivity, small volume changes on phase transformation, small vapor pressure at operating temperatures, and/or congruent melting. For some applications, the phase-change molecules are selected to have given kinetic properties, such as a high nucleation rate, and/or a high rate of crystal growth. For some applications, the phase-change molecules are selected to have given chemical properties, such as chemical stability, reversibility of the phase-change cycle without degradation of the molecules after a large number of phase-change cycles, non-corrosiveness, and/or non-toxicity.

For some applications, organic phase-change material molecules are used for cluster 42. For example, paraffin and/or fatty acid molecules may be used in cluster 42. For some applications, organic molecules are used in cluster 42 because the organic phase change-molecules freeze without substantial super cooling, are able to melt congruently, have self-nucleating properties, do not segregate, are chemically stable, have a high heat of fusion, and/or for a different reason.

For some applications, one or more of the following phase-change molecules are used in cluster 42: Octadecane (CAS Number 593-45-3), Lauric acid (CAS No: 143-07-7), Myristic acid (CAS No: 544-63-8), Palmitic acid (CAS No: 57-10-3), Heptadecanoic acid (CAS No: 506-12-7), Stearic acid (CAS No: 57-11-4), Arachidic acid (CAS No: 506-30-9), Behenic acid (Cas No: 112-85-6) Trimethylolethane (CAS No:77-85-0), Stearamine (Octadecylamine) (Sigma-74750), Cetylamine (Hexadecylamine) (Sigma-445312).

For some applications, one or more of the phase-change materials that appear in Table 1, and/or in Table 2 (both which tables are shown hereinabove), are used as the phase-change material of cluster 42. Typically, a phase-change material is selected as the phase-change material, on the basis of the phase change temperature of the phase-change material. For some applications, other melting temperatures and corresponding materials are used.

For some applications, one or more of the following organic phase-change materials is used for phase-change material 42: crude oil, paraffin produced by the Fischer-Tropsch process, and an organic material having saturated, unsaturated, straight, or branched carbon chain molecules. The phase-change material may include, for example, trilaurin, trimyristin, tripalmitin, tristearin, and/or any suitable type of paraffin or paraffin wax.

The melting temperature of the phase-change material is typically 45 C to 60 C, or 60 C to 80 C. The phase change which the phase change material undergoes, is typically solid to liquid, solid to gel, or gel to liquid.

Reference is now made to FIG. 3, which is a graph showing experimental results of five pieces of tissue that were heated in a control experiment, conducted in accordance with some applications of the present invention. Five pieces of tissue, each weighing 13 grams, were cut from either turkey liver, chicken chest, or calf liver. The pieces of tissue were each mounted on a polystyrene board, using mounting pins, at a distance of 55 mm from an RF generator. The RF generator irradiated each piece of tissue for several time intervals: 30 sec, 50 sec, 80 sec, and 100 sec. The temperature of each of the pieces of tissue was measured immediately after the tissue was irradiated, using a k-type thermocouple. The maximum temperature in the tissue following the irradiation of the tissue is shown in Table 4, and is plotted on the graph of FIG. 3. The ambient temperature was 24.2 C-25 C. The irradiation of the pieces was done in accordance with the following protocol:

Piece 1—A 40 mm reflector was mounted on the RF generator in order to concentrate the RF energy on a specific area, and, in doing so, reduce damage to peripheral portions of the tissue.

Piece 2—A 30 mm reflector was mounted on the RF generator.

Piece 3—No reflector was mounted on the RF generator.

Piece 4—No reflector was mounted on the RF generator. Carbon cylinders, each cylinder having a diameter of 0.9 mm and a length of 20 mm to 40 mm, were inserted into the tissue at intervals of 10 mm.

Piece 5—No reflector was mounted on the RF generator. Carbon cylinders, each cylinder having a diameter of 2 mm and a length of 20 mm to 40 mm, were inserted into the tissue at intervals of 10 mm.

TABLE 4

Initial and final temperatures of control group

| PIECE | TIME INTERVAL (s) | INITIAL TEMPERATURE (° C.) | MAXIMUM FINAL TEMPERATURE (° C.) |
| --- | --- | --- | --- |
| 1 | 30 | 24.0 | 24.8 |
| 1 | 50 | 24.8 | 25.4 |
| 1 | 80 | 25.4 | 38.4 |
| 1 | 100 | 23.7 | 47.5 |
| 2 | 30 | 19.8 | 23.1 |
| 2 | 50 | 23.1 | 30.4 |
| 2 | 80 | 28.7 | 42.2 |
| 2 | 100 | 35.6 | 50.3 |
| 3 | 30 | 25.5 | 27.4 |
| 3 | 50 | 28.6 | 34.6 |
| 3 | 80 | 32.7 | 66.3 |
| 3 | 100 | 55.0 | 95.8 |
| 4 | 30 | 23.3 | 36.3 |
| 4 | 50 | 35.2 | 48.9 |
| 4 | 80 | 47.5 | 73.2 |
| 4 | 100 | 71.2 | 122.3 |
| 5 | 30 | 23.8 | 37.9 |
| 5 | 50 | 37.3 | 50.3 |
| 5 | 80 | 48.7 | 85.8 |
| 5 | 100 | 73.2 | 143.4 |

As is seen in FIG. 3, use of carbon cylinders in the tissue accelerates the heating of the tissue, and a 2 mm diameter cylinder causes faster heating than a 0.9 mm diameter cylinder. It is noted that experiments were conducted on the control group, in which smaller carbon cylinders, having diameters of 0.3 mm, 0.5 mm, and 0.7 mm were inserted into the tissue and the tissue was heated. The smaller carbon cylinders were observed to have little effect on the heating of the tissue, indicating that carbon cylinders that are smaller than a minimum size (e.g., 0.9 mm in diameter) are not good RF energy absorbers when placed inside tissue. In addition, use of a reflector retards heating of the tissue, and a larger reflector retards the heating more than a smaller reflector.

Reference is now made to FIG. 4, which is a graph showing experimental results of four pieces of tissue that were injected with phase-change materials and were heated, in accordance with some applications of the present invention. Four pieces of tissue, each weighing 13 grams, were cut from either turkey liver, chicken chest, or calf liver. The pieces of tissue were each mounted on a polystyrene board, using mounting pins, at a distance of 55 mm from an RF generator. A 40 mm reflector was mounted on the RF generator and the generator irradiated each piece of tissue for several time intervals: 30 sec, 50, sec, 80 sec, 100 sec, and 180 sec. The maximum temperature of the tissue following the irradiation of the tissue was measured using a k-type thermocouple, and the results shown in Table 5, and are plotted on the graph of FIG. 4. The ambient temperature was 24.2 C-25 C. The irradiation of the pieces was done in accordance with the following protocol:

Piece 1—The piece was injected with 5 cc of a trilaurin-based mixture, comprising 0.8 g of trilaurin, 0.1 g of Tween 80, 0.16 g of lecithin Epikuron 200, and 20 g of water.

Piece 2—The piece was injected with 5 cc of a trimyristin-based mixture, comprising 0.8 g of trimyristin, 0.1 g of Tween 80, 0.16 g of lecithin Epikuron 200, and 20 g water.

Piece 3—The piece was injected with 5 cc of a tripalmitin-based mixture, comprising 0.8 g of tripalmitin, 0.1 g of Tween 80, 0.16 g of lecithin Epikuron 200, and 20 g of water.

Piece 4—The piece was injected with 5 cc of a tristearin-based mixture, comprising 0.8 g of tristearin, 0.1 g of Tween 80, 0.16 g of lecithin Epikuron 200 and 20 g of water.

TABLE 5

Initial and final temperatures of test group

| PIECE | TIME INTERVAL (s) | INITIAL TEMPERATURE (° C.) | MAXIMUM FINAL TEMPERATURE (° C.) |
|---|---|---|---|
| 1 | 30 | 24.5 | 29.2 |
| 1 | 50 | 28.5 | 35.4 |
| 1 | 80 | 34.2 | 41.8 |
| 1 | 100 | 40.6 | 45.7 |
| 1 | 180 | 44.2 | 45.7 |
| 2 | 30 | 24.8 | 29.7 |
| 2 | 50 | 29.1 | 35.2 |
| 2 | 80 | 33.9 | 42.7 |
| 2 | 100 | 41.1 | 55.2 |
| 2 | 180 | 54.7 | 55.2 |
| 3 | 30 | 25.0 | 31.1 |
| 3 | 50 | 29.8 | 36.9 |
| 3 | 80 | 35.6 | 44.3 |
| 3 | 100 | 43.4 | 65.4 |
| 3 | 180 | 63.2 | 65.4 |
| 4 | 30 | 28.6 | 35.9 |
| 4 | 50 | 34.6 | 42.1 |
| 4 | 80 | 40.3 | 49.9 |
| 4 | 100 | 49.2 | 75 |
| 4 | 180 | 74.1 | 75 |

Use of phase-change materials is seen in FIG. 4 to produce prolonged periods of stable maximum tissue temperature during continued application of energy.

Reference is now made to FIG. 5, which is a graph showing experimental results of four pieces of tissue that were injected with phase-change materials and into which carbon cylinders were inserted, in accordance with some applications of the present invention. Four pieces of tissue, each weighing 13 grams, were cut from either turkey liver, chicken chest, or calf liver. Carbon cylinders, each cylinder having a diameter of 0.9 mm and a length of 20 mm to 40 mm were inserted into each of the pieces of tissue at intervals of 10 mm. The pieces of tissue were each mounted on a polystyrene board, using mounting pins, at a distance of 55 mm from an RF generator. A 40 mm reflector was mounted on the RF generator. Each of the pieces of tissue was heated for several time intervals. The maximum temperature measured within each of the pieces of tissue following each of these time intervals was measured using a k-type thermocouple, and is shown in Table 6, and plotted on the graph of FIG. 5. The ambient temperature was 24.2 C-25 C. The irradiation of the pieces was done in accordance with the following protocol:

Piece 1—The piece was injected with 5 cc of a trilaurin-based mixture, comprising 0.8 g of trilaurin, 0.1 g of Tween 80, 0.16 g of lecithin Epikuron 200, and 20 g of water. The piece was heated for time intervals of 30 sec, 50 sec, and 180 sec.

Piece 2—The piece was injected with 5 cc of a trimyristin-based mixture, comprising 0.8 g of trimyristin, 0.1 g of Tween 80, 0.16 g of lecithin Epikuron 200, and 20 g water. The piece was heated for time intervals of 30 sec, 50 sec, and 180 sec.

Piece 3—The piece was injected with 5 cc of a tripalmitin-based mixture, comprising 0.8 g of tripalmitin, 0.1 g of Tween 80, 0.16 g of lecithin Epikuron 200, and 20 g of water. The piece was heated for time intervals of 30 sec, 50 sec, 80 sec, and 180 sec.

Piece 4—The piece was injected with 5 cc of a tristearin-based mixture, comprising 0.8 g of tristearin, 0.1 g of Tween 80, 0.16 g of lecithin Epikuron 200 and 20 g water. The piece was heated for time intervals of 30 sec, 50 sec, 80 sec, 100 sec, and 180 sec.

TABLE 6

Initial and final temperatures of test group, with carbon cylinders

| PIECE | TIME INTERVAL (s) | INITIAL TEMPERATURE (° C.) | MAXIMUM FINAL TEMPERATURE (° C.) |
|---|---|---|---|
| 1 | 30 | 24.5 | 37.2 |
| 1 | 50 | 36.1 | 45.7 |
| 1 | 180 | 43.2 | 45.7 |
| 2 | 30 | 24.5 | 37.1 |
| 2 | 50 | 36.1 | 49.6 |
| 2 | 180 | 46.3 | 55.2 |
| 3 | 30 | 24.8 | 37.2 |
| 3 | 50 | 36.8 | 49.1 |
| 3 | 80 | 47.1 | 65.4 |
| 3 | 180 | 63.9 | 65.4 |
| 4 | 30 | 24.1 | 37.1 |
| 4 | 50 | 34.8 | 48.6 |
| 4 | 80 | 47.7 | 73.4 |
| 4 | 100 | 73.2 | 75.0 |
| 4 | 180 | 68.1 | 75.0 |

As is seen in FIG. 5, the piece injected with the trilaurin-based mixture reached its phase-change temperature quickly, and maintained this temperature throughout the experiment. The pieces injected with other phase-change materials, while taking somewhat longer to reach their respective phase-change temperatures, also maintained their temperatures at their respective phase-change temperatures throughout the experiment.

The following points may be observed from the experimental results illustrated by the graphs of FIGS. 3-5:

(a) Injection of a phase-change material into tissue can inhibit the tissue from being heated above a given temperature for a significant period of time. During this time, the phase-change material is absorbing heat energy as the latent heat of fusion of the phase change.

(b) Inserting carbon cylinders into tissue shortens the length of time required to heat the tissue to a given temperature, ceteris paribus, provided that the carbon cylinders have a diameter that is greater than a minimum diameter, e.g. 0.9 mm. It is noted that other materials that are good energy absorbers, such as graphite and metals, may be used to shorten the length of time required to heat the tissue to a given temperature.

Therefore, for some applications of the invention, as described hereinabove, a phase-change material is inserted into a subject's tissue to facilitate the heating of the tissue to a given temperature and to inhibit the tissue from being heated above the given temperature. For some applications, an energy absorbing element 36 is inserted into a subject's tissue to facilitate the heating of the tissue, for example, by drawing energy from a heating device to the tissue, as described hereinabove. Typically, energy absorbers that are biocompatible and that do not show artifacts in during imaging (e.g., X ray or MRI imaging) of the tissue, such as carbon or graphite cylinders, are inserted into the tissue. For some applications, carbon cylinders, each of the cylinders having a diameter that is at least 0.9 mm, are inserted into the tissue. For some applications, an implantable, biocompatible metal, such as nitinol, stainless steel, cobalt and/or chromium, is used as an energy absorbing element.

For some applications, energy is transmitted toward clusters of phase-change molecules that are coupled to molecules (such as glucose molecules), which, in turn, are coupled to cancer cells. In response to the energy striking the clusters of phase-change molecules, the temperature of the region in which the phase-change molecules are disposed rises, but does not rise above the phase-change temperature of the phase-change molecules. This is because, at the phase-change temperature, the heat that is transmitted toward the region is absorbed by the phase-change molecules as latent heat. The heating of the phase-change molecules typically heats the cancer cells, thereby killing the cancer cells.

Figure 6:
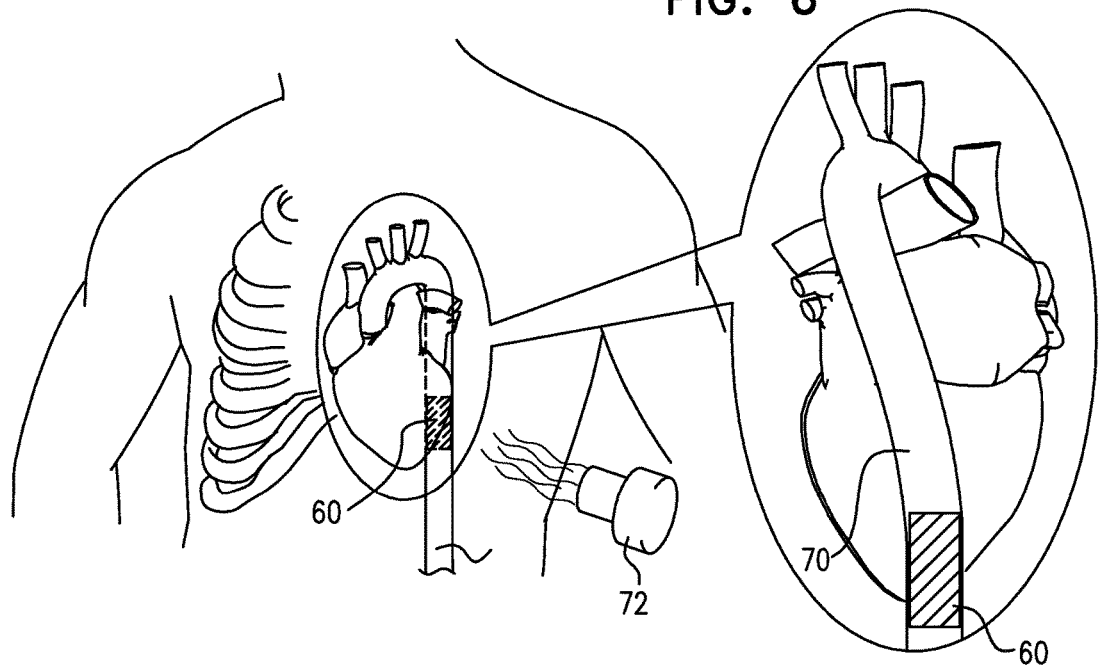
FIG. 6 is a schematic illustration of an implantable element implanted inside a blood vessel of a subject.

Reference is now made to FIG. 6, which is a schematic illustration of an implantable element 60 implanted within a portion of a subject's body, for example, a blood vessel 70 of the subject. The element includes a shape-memory material having a transformation temperature. The implantable element performs a first therapeutic function with respect to the blood vessel when the shape-memory material is in a first shape. An energy applicator 72 changes the shape-memory material from the first shape to a second shape, by raising a temperature of the shape-memory material to the transformation temperature. The second shape is maintained even after energy applicator 72 no longer applies energy to implantable element 60, and the temperature of implantable element 70 returns to body temperature. When the shape-memory material is in the second shape, the implantable element performs a second therapeutic function with respect to the portion, the second therapeutic function being qualitatively different from the first therapeutic function.

Typically, energy applicator 72 is an energy applicator as is known in the art, for example, an RF generator, an ultrasound transducer, and/or a magnetic field generator. Further typically, element 60 contains a shape-memory material as is known in the art, for example, nitinol, copper-zinc-aluminum-nickel, and/or copper-aluminum-nickel.

Figure 7A:
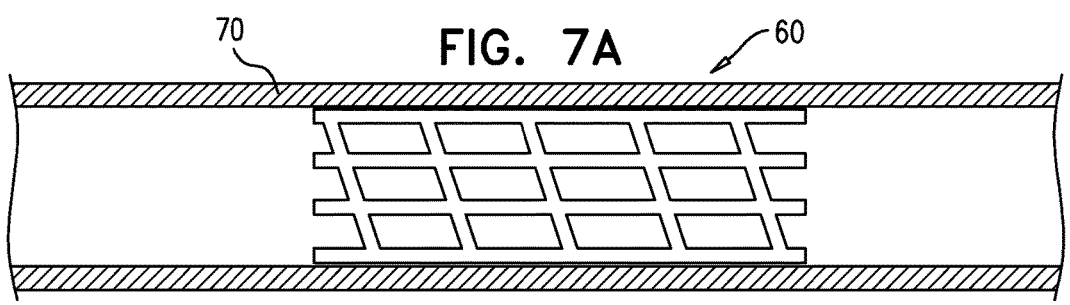
FIG. 7A is a schematic illustration of the implantable element in a first configuration, in accordance with some applications of the present invention.
Figure 7B:
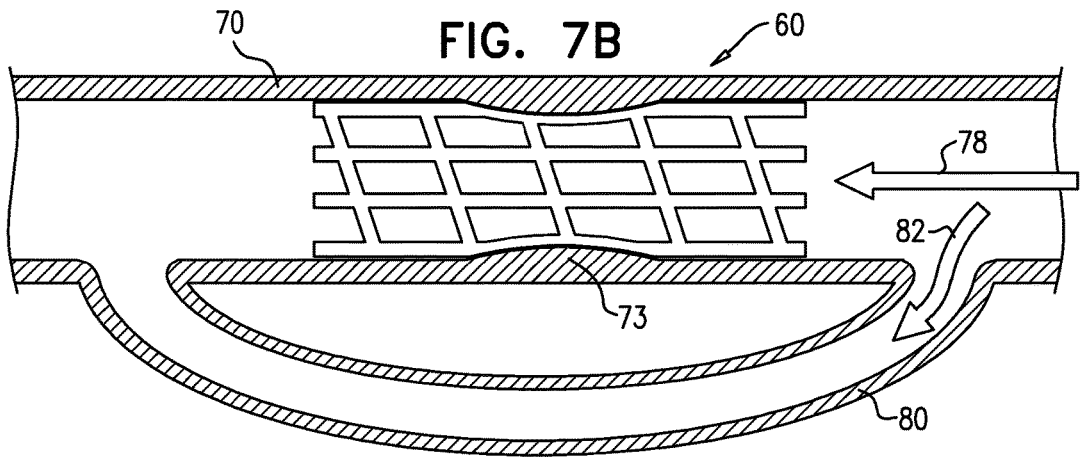
FIG. 7B is a schematic illustration of the implantable element in a second configuration, in accordance with some applications of the present invention.

Reference is now made to FIGS. 7A-B, which are schematic illustrations of implantable element 60 in respective first and second configurations, in accordance with some applications of the present invention. For some applications, implantable element 60 is a stent (as shown), which, in a first configuration thereof, supports a narrowed blood vessel 70, in order to open, and/or widen the blood vessel, as shown in FIG. 7A. Implantable element 60 is typically maintained in its first configuration for a prolonged period (e.g., weeks or months, or a different period of time), until a desired effect of the stent has been attained. Subsequently, energy applicator 72 raises the temperature of the stent to the transformation temperature of the shape change material of the stent, and the shape of the stent changes to the shape of a venturi tube, as shown in FIG. 7B, i.e., a central portion of the stent narrows.

For some applications, when the stent is in the second configuration, it causes a controlled narrowing of blood vessel 70, region 73 of the blood vessel wall collapsing to the outer wall of the stent. As a result of the narrowing of the blood vessel, blood flow (indicated by arrow 78) upstream of region 73 is impeded. In response to sensing impeded blood flow, the body generates a new blood vessel 80 (not to scale), which circumvents the constriction of region 73. When the new blood vessel has generated, the blood flows through the new blood vessel, in the direction of arrow 82. This general physiological response of the body to an implanted venturi stent is described in PCT Publication WO 03/028522 to Ben Muvhar, which is incorporated herein by reference.

For some applications of the present invention, a stent that contains a shape-memory material is implanted in an artery of a subject's brain, for example, a cerebral artery of the subject. In a first configuration thereof, the stent supports the artery in order to open, and/or widen the artery. Subsequently, the temperature of the stent is raised to the transformation temperature of the shape-memory material of the stent, causing the stent to expand. The expanded stent is used to facilitate drug delivery across the subject's blood brain barrier, by increasing the intercellular gaps of the blood brain barrier.

In a further application of the present invention, a stent that contains a shape-memory material is implanted in a subject's esophagus, in a vicinity of an esophageal tumor. In a first configuration thereof, the stent supports the esophagus in order to open the esophagus in the vicinity of the tumor. Typically, the stent is configured to have a degree of flexibility that is sufficient to facilitate peristalsis through the esophagus, while the stent is disposed in the esophagus in the first configuration thereof. Subsequently, the temperature of the stent is raised to the transformation temperature of the shape-memory material of the stent, causing the stent to expand. Typically, the stent is expanded by a healthcare professional, in response to the tumor growing to a size such that it interferes with the ingestion of food by the subject. The expanded stent pushes back the tumor, thereby widening the esophagus.

The scope of the present invention includes a shape-memory material that is implanted in a subject's bone, the bone requiring elongation, for example, subsequent to surgery on the bone. The shape-memory material is surgically coupled to the bone. Subsequently (for example, a day, a week or a month after the implantation), the temperature of the shape-memory material is raised, causing the shape-memory material to expand, and, consequently, causing the bone to lengthen. The shape-memory material is further expanded by repeatedly heating the shape-memory material (for example, once every day, every week or every month, or as required), during the period of the bone elongation.

Reference is now made to FIGS. 8A-B, which are schematic illustrations of a portion 90 of a drug pump, in accordance with some applications of the present invention. Portion 90 includes a drug chamber 92, a shape-memory material 94, and a separator 96 (e.g., a piston that separates the shape-memory material and the drug chamber). For some applications, in order to release a given quantity of a drug 98 from chamber 92, the shape-memory material is heated to its transformation temperature, for a given time period. Upon heating the shape-memory material to the transformation temperature (e.g., a temperature of 40-60 C), the shape-memory material expands, as it undergoes a shape change, and releases the given quantity of the drug by advancing separator 96 through a given distance, as shown in FIG. 8B.

For some applications, the heating of the shape-memory material is terminated before the shape-memory material has fully undergone its shape-change. In a subsequent interaction, in order to dispense more of the drug, the shape-memory material is again heated to its transformation temperature, thereby causing the shape-memory material to further expand, as it continues to undergo the shape change, thus releasing more of the drug.

Typically, energy is applied to shape-memory material 94 by irradiating the shape-memory material, for example, using an RF generator, an ultrasound transducer, and/or a magnetic field generator. Further typically, shape-memory material 94 is a shape-memory material that is known in the art, for example, nitinol, copper-zinc-aluminum-nickel, and/or copper-aluminum-nickel. For some applications, the shape-memory material expands by 5 percent to 25 percent, e.g. 8 percent to 12 percent, in each interaction in which the shape-memory material is heated.

For some applications, portion 90 comprises a portion of an implantable drug pump, the drug pump being as known in the art. For some applications, portion 90 is used to administer insulin to a diabetic subject. Alternatively or additionally, the portion is used to administer a chemotherapy agent to a subject suffering from cancer.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
   a stent configured to be implanted within a body of a subject, the stent being shaped to define a hollow volume therein; and
   a phase-change material:
      disposed within the hollow volume, and
      configured to absorb heat from the stent by absorbing latent heat of fusion resulting from a phase-change of the phase-change material selected from the group consisting of: wax to liquid, solid to liquid, solid to gel, and gel to liquid, in response to the stent being heated.

2. The apparatus according to claim 1, wherein the phase-change material is hermetically sealed within the stent.

3. The apparatus according to claim 1, further comprising an energy transmission unit, configured to heat the stent by transmitting, toward the stent, energy that selectively heats the stent.

4. The apparatus according to claim 1, wherein the stent:
   is tubular,
   has (i) an inner surface that defines a main longitudinal lumen of the stent, and (ii) an outer surface that faces radially outward, and
   is shaped to define the hollow volume between the inner surface and the outer surface, the phase-change material being disposed within the hollow volume that is defined between the inner surface and the outer surface.

5. The apparatus according to claim 4, wherein the phase-change material is hermetically sealed within the stent.

6. The apparatus according to claim 1, wherein the phase-change material has a phase-change temperature of 45 C to 60 C.

* * * * *